(12) United States Patent
McHugh et al.

(10) Patent No.: US 10,905,313 B2
(45) Date of Patent: Feb. 2, 2021

(54) PRESSURE MONITORING APPARATUS, A CATHETER AND A METHOD FOR MONITORING PRESSURE IN A LIQUID

(71) Applicant: Crospon Limited, Galway (IE)

(72) Inventors: Adrian McHugh, Galway (IE); Richard Kiely, Galway (IE)

(73) Assignee: CROSPON LIMITED, Galway (IE)

(*) Notice: Subject to any disclaimer, the term of this patent is extended or adjusted under 35 U.S.C. 154(b) by 101 days.

(21) Appl. No.: 16/312,399

(22) PCT Filed: Jun. 22, 2017

(86) PCT No.: PCT/IE2017/000011
§ 371 (c)(1),
(2) Date: Dec. 21, 2018

(87) PCT Pub. No.: WO2017/221223
PCT Pub. Date: Dec. 28, 2017

(65) Prior Publication Data
US 2019/0335980 A1 Nov. 7, 2019

(30) Foreign Application Priority Data

Jun. 23, 2016 (IE) .................................. S2016/0169

(51) Int. Cl.
*A61B 1/00* (2006.01)
*A61M 25/10* (2013.01)
(Continued)

(52) U.S. Cl.
CPC ............ *A61B 1/0014* (2013.01); *A61B 1/018* (2013.01); *A61B 5/02141* (2013.01);
(Continued)

(58) Field of Classification Search
CPC ... A61B 1/0014; A61B 1/018; A61B 5/02141; A61B 5/1076; A61B 5/021;
(Continued)

(56) References Cited

U.S. PATENT DOCUMENTS 4,261,208 A * 4/1981 Hok ..................... A61B 5/0215
338/38
4,291,575 A 9/1981 Frissora
(Continued)

FOREIGN PATENT DOCUMENTS

| EP | 2 716 323 | 4/2014 |
|---|---|---|
| WO | WO 89/04631 | 6/1989 |
| WO | WO-9604846 A1 * | 2/1996 ........... A61B 5/0215 |

*Primary Examiner* — Jonathan M Dunlap
(74) *Attorney, Agent, or Firm* — Pearl Cohen Zedek Latzer Baratz LLP

(57) ABSTRACT

A pressure monitoring apparatus (1) for monitoring pressure of a liquid (4) in a vessel (2) comprises a housing (3) within which an airtight gas chamber (6) is formed. A pressure sensor (8) is located in the housing (3) monitors the pressure of a gas in the gas chamber (6). A conduit (12) having a communicating bore (16) of total length $L_t$ communicates the gas chamber (6) with the vessel (2). As the pressure of the liquid in the vessel (2) increases, a liquid/gas interface meniscus (20) travels along a working length $L_w$ of the communicating bore (16) from the second end (15) thus increasing the pressure in the gas chamber (6) to the pressure of the liquid, which is monitored by the pressure sensor (8). The total length $L_t$ of the conduit (12) is greater than the working length $L_w$ of the conduit (12) to avoid the liquid/gas interface meniscus (20) reaching the first end (14) of the communicating bore (16). The pressure monitoring apparatus (1) may also be mounted at the distal end (33) of a balloon catheter (30) for monitoring the pressure of a liquid inflating medium inflating the balloon (35) of the balloon catheter (30), which may be an electrically conductive (Continued)

Figure 3:
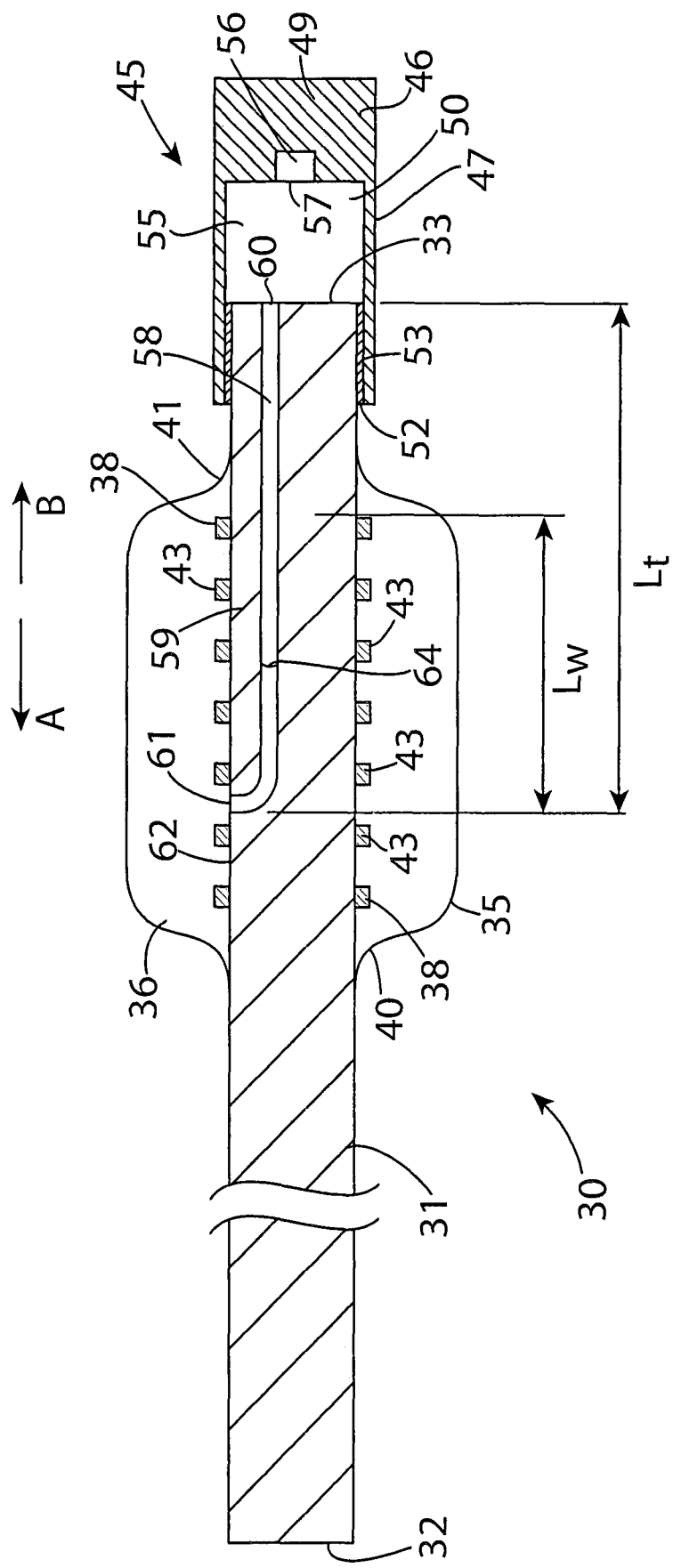

liquid, with the gas isolating the pressure sensor (8) from the liquid inflating medium.

19 Claims, 6 Drawing Sheets

(51) Int. Cl.

| | | |
|---|---|---|
| *A61B 1/018* | (2006.01) | |
| *A61B 5/021* | (2006.01) | |
| *A61B 5/107* | (2006.01) | |
| *A61M 25/00* | (2006.01) | |
| *A61B 90/00* | (2016.01) | |
| *A61B 5/053* | (2006.01) | |
| *G01L 9/00* | (2006.01) | |
| *G01L 19/00* | (2006.01) | |
| *A61B 5/0215* | (2006.01) | |

(52) U.S. Cl.
CPC ..... *A61B 5/1076* (2013.01); *A61M 25/10184* (2013.11); *A61B 5/021* (2013.01); *A61B 5/0215* (2013.01); *A61B 5/0538* (2013.01); *A61B 90/06* (2016.02); *A61B 2090/064* (2016.02); *A61B 2562/0247* (2013.01); *A61M 25/10188* (2013.11); *A61M 2025/0001* (2013.01); *G01L 9/00* (2013.01); *G01L 19/0007* (2013.01)

(58) Field of Classification Search
CPC ................ A61B 5/0538; A61B 5/0215; A61B 2562/0247; A61B 90/06; A61B 2090/064; A61M 25/10184; A61M 25/10188; A61M 25/00; A61M 2025/0001; A61M 2562/0247; G01L 9/00; G01L 19/0007
See application file for complete search history.

(56) References Cited

U.S. PATENT DOCUMENTS

| | | | |
|---|---|---|---|
| 4,297,890 A * | 11/1981 | Hok ................... | A61B 5/0215 338/38 |
| 4,413,528 A * | 11/1983 | Hok ................... | A61B 5/0215 338/38 |
| 4,459,841 A * | 7/1984 | Hok ....................... | G01L 11/00 600/486 |
| 4,966,161 A * | 10/1990 | Wallace ................. | A61B 5/035 600/561 |
| 5,450,853 A * | 9/1995 | Hastings ............... | A61B 5/0215 600/488 |
| 6,910,377 B1 * | 6/2005 | Richter ................. | G01F 11/284 73/290 R |
| 2002/0072647 A1 * | 6/2002 | Schock ................ | A61B 5/0215 600/18 |
| 2008/0036615 A1 | 2/2008 | Lyall, III | |
| 2013/0030262 A1 * | 1/2013 | Burnett ................ | A61B 5/0402 600/309 |
| 2015/0305633 A1 * | 10/2015 | McCaffrey ........... | A61B 5/6852 600/486 |
| 2016/0007851 A1 * | 1/2016 | Araci ................... | A61B 8/0841 600/403 |

* cited by examiner

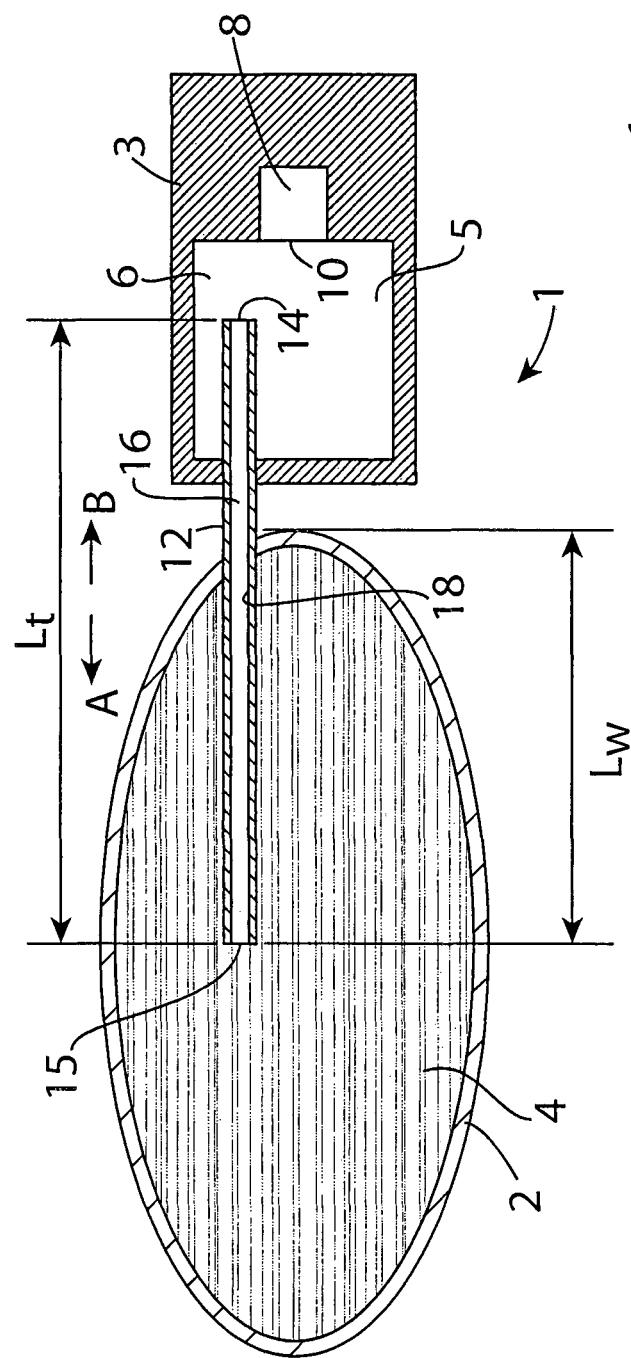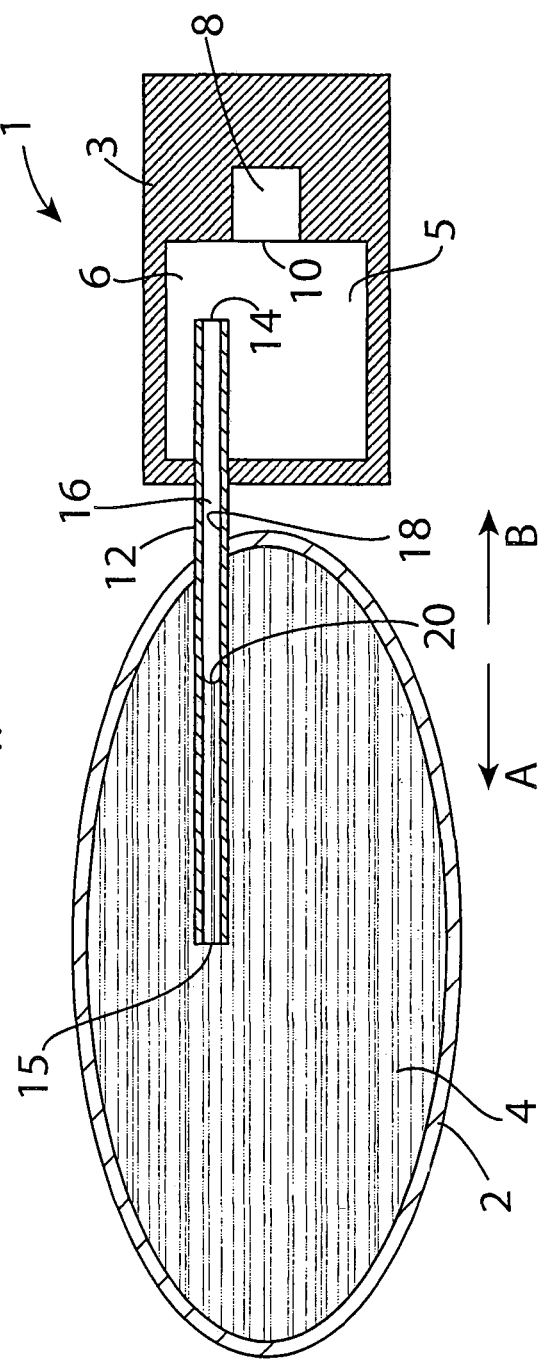

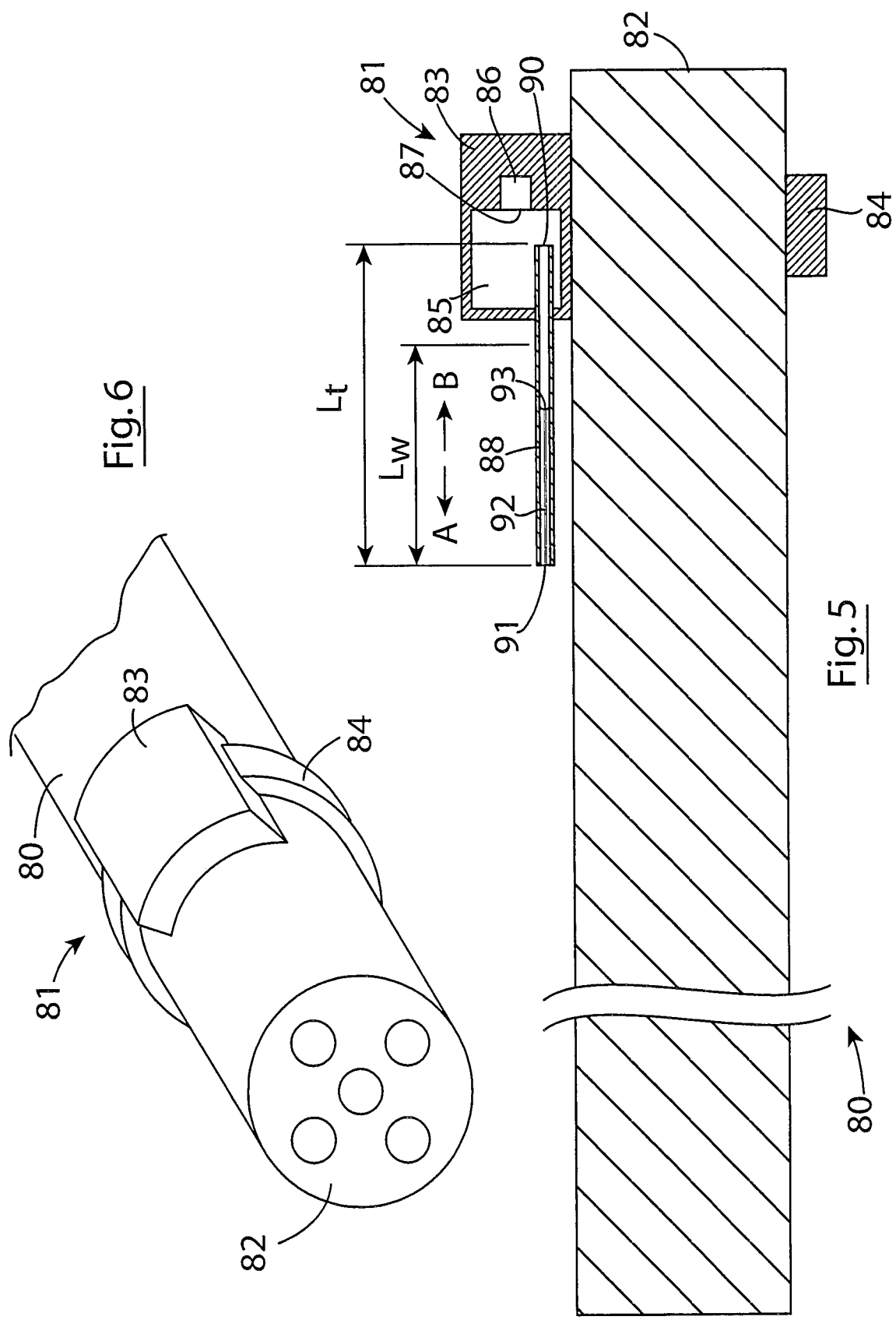

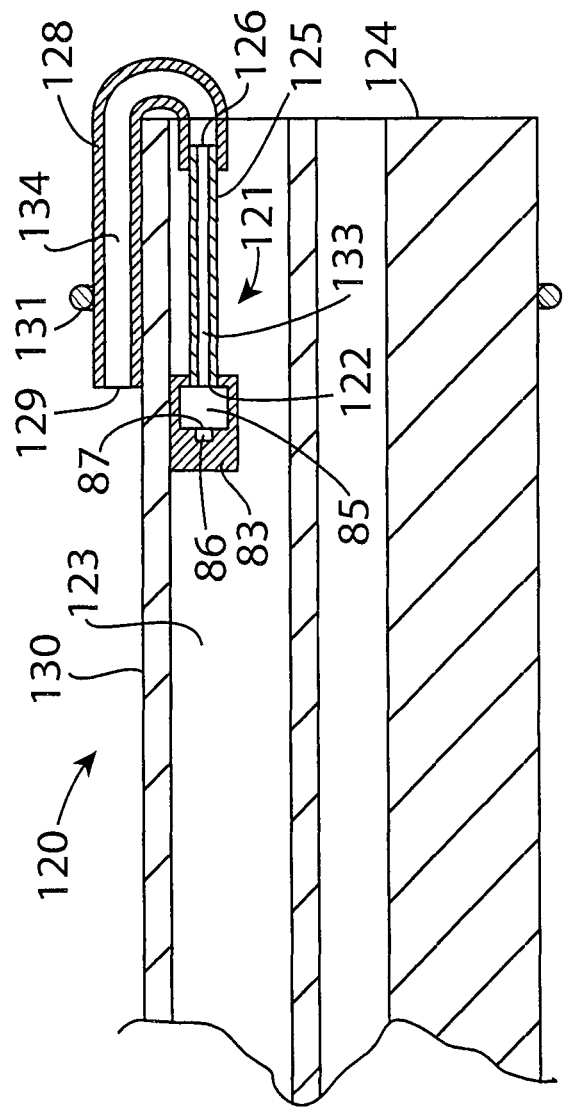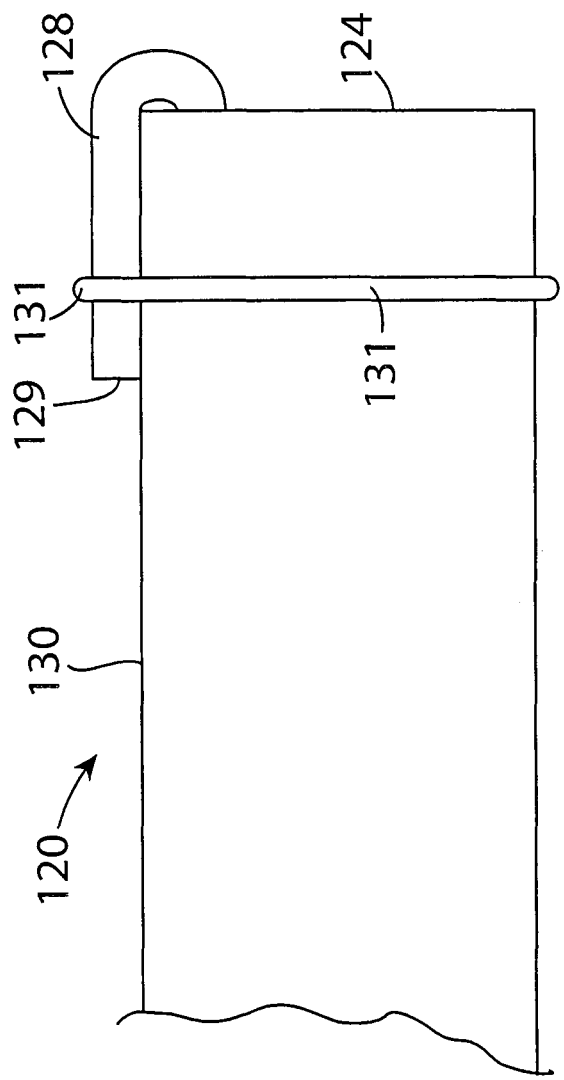

PRESSURE MONITORING APPARATUS, A CATHETER AND A METHOD FOR MONITORING PRESSURE IN A LIQUID

CROSS-REFERENCE TO RELATED APPLICATIONS

This application is a National Phase Application of PCT International Application No. PCT/IE2017/000011, International Filing Date Jun. 22, 2017, claiming priority of IE Patent Application(s) No(s). S2016/0169, filed Jun. 23, 2016, each of which are hereby incorporated by reference.

The present invention relates to a pressure monitoring apparatus, and in particular, to a pressure monitoring apparatus for monitoring pressure in a liquid, and the invention also relates to a method for monitoring pressure in a liquid. Additionally, the invention relates to a catheter.

Pressure sensors are regularly used for monitoring the pressure of a liquid. Such pressure sensors may be mechanical, electrical, electronic, and indeed solid state devices. Electrical, electronic and solid state device pressure sensors, in general, tend to be relatively accurate, and in general, are more accurate than mechanical and other types of pressure sensors, and furthermore, are in general, more convenient to use. However, one problem with electrical and electronic pressure sensors and solid state pressure sensors is that they cannot be placed in direct contact with fluids which are electrically conductive. In particular, such pressure sensors are unsuitable for measuring pressure directly in liquids, and in particular, electrically conductive liquids.

In general, when it is desired to use such electrical, electronic and solid state pressure sensors for monitoring pressure in an electrically conductive liquid, it is essential that the electrically conductive liquid be separated from the sensor. This, in general, is achieved by placing a diaphragm or other suitable physical membrane between the liquid and the pressure sensor for isolating the pressure sensor from the liquid. This results in a number of disadvantages. In particular, the response time of the pressure sensor is reduced due to inherent delays in movement of the diaphragm or other such membrane, and secondly, a reduction in the accuracy of the pressure read by the pressure sensor may also occur. In cases where the diaphragm or other such membrane is located to separate a gas or air chamber within which the pressure sensor is located from the liquid, the amount of gas or air between such a diaphragm or a membrane and the pressure sensor also serves to dictate the pressure range within which pressure can be monitored. This is of particular relevance when the space available to house a pressure sensor is limited, but the pressure range within which pressure is to be monitored is relatively large.

There is therefore a need for a pressure monitoring apparatus which addresses at least some of these problems, and there is also a need for a pressure monitoring apparatus for monitoring the pressure in a liquid which produces relatively accurate results with minimum time delays.

The present invention is directed towards providing a pressure monitoring apparatus for monitoring pressure in a liquid, a method for monitoring pressure in a liquid, and a catheter.

According to the invention there is provided a pressure monitoring apparatus for monitoring pressure in a liquid, the pressure monitoring apparatus comprising a pressure sensor having a pressure sensing interface communicating directly with a gas in a gas chamber, an elongated communicating bore communicating the gas chamber with the liquid, the pressure of which is to be monitored, the communicating bore having a working length along which a liquid/gas interface meniscus travels in response to pressure variation in the liquid, the working length of the communicating bore being of length to contain the travel of the liquid/gas interface meniscus within the working range of pressures being monitored, the transverse cross-sectional area of the communicating bore along the working length thereof being such as to prevent the passage of liquid past or through the liquid/gas interface meniscus, and to prevent the passage of gas past or through the liquid/gas interface meniscus.

The invention also provides a catheter extending between a proximal end and a distal end, and comprising a pressure monitoring apparatus according to the invention.

Additionally, the invention provides a catheter extending between a proximal end and a distal end, and comprising a pressure monitoring apparatus for monitoring pressure in a liquid, the pressure monitoring apparatus comprising a pressure sensor having a pressure sensing interface communicating directly with a gas in a gas chamber, an elongated communicating bore extending from the gas chamber to communicate the gas chamber with the liquid, the pressure of which is to be monitored, the communicating bore having a working length along which a liquid/gas interface meniscus travels in response to pressure variation in the liquid, the working length of the communicating bore being of length to contain the travel of the liquid/gas interface meniscus within the working range of pressures being monitored, the transverse cross-sectional area of the communicating bore along the working length thereof being such as to prevent the passage of liquid past or through the liquid/gas interface meniscus, and to prevent the passage of gas past or through the liquid/gas interface meniscus.

Further the invention provides a method for monitoring pressure in a liquid, the method comprising communicating a gas chamber containing a gas therein with the liquid through an elongated communicating bore, the communicating bore having a working length along which a liquid/gas interface meniscus travels in response to pressure variation in the liquid, the working length of the communicating bore being of length to contain the travel of the liquid/gas interface meniscus within the working range of pressures being monitored, and the working length of the communicating bore being of transverse cross-sectional area such as to prevent the passage of liquid past or through the liquid/gas interface meniscus, and to prevent the passage of gas past or through the liquid/gas interface meniscus, and monitoring the pressure of the gas in the gas chamber.

In one aspect of the invention the transverse cross-sectional area of the communicating bore along the working length thereof is such that the surface tension force induced in the liquid/gas interface meniscus is such as to prevent the passage of liquid past or through the liquid/gas interface meniscus and to prevent the passage of gas past or through the liquid/gas interface meniscus.

In another aspect of the invention the surface of the communicating bore along the working length thereof is such that the surface tension induced in the liquid/gas interface meniscus is such as to prevent the passage of liquid past or through the liquid/gas interface meniscus and to prevent passage of gas past or through the liquid/gas interface meniscus.

In a further aspect of the invention the transverse cross-sectional area of the communicating bore along the working length thereof is such that a combination of the cohesive force within the liquid and the adhesive force between the liquid and the material through which the communicating bore extends is sufficient to overcome any driving forces which would result in the passage of the liquid past or through the to liquid/gas interface meniscus and the passage of gas past or through the liquid/gas interface meniscus.

Preferably, the transverse cross-sectional area of the communicating bore along the working length thereof is such that a combination of the cohesive force within the liquid and the adhesive force between the liquid and the material through which the communicating bore extends is sufficient for the periphery of the liquid/gas interface meniscus to extend completely around the interior of the transverse cross-sectional area of the working length of the communicating bore.

Advantageously, the transverse cross-sectional area of the communicating bore along the working length thereof is such that the surface tension of the liquid, combined with the adhesive forces between the liquid and the material through which the communicating bore extends are sufficient to prevent the passage of liquid past or through the liquid/gas interface meniscus, and to prevent the passage of gas past or through the liquid/gas interface meniscus.

In one aspect of the invention the surface tension in the liquid/gas interface meniscus in the working length of the communicating bore is such as to prevent the passage of liquid past or through the liquid/gas interface meniscus, and to prevent the passage of gas past or through the liquid/gas interface meniscus.

In another aspect of the invention the transverse cross-sectional area of the communicating bore along the working length thereof does not exceed 20 mm$^2$. Preferably, the transverse cross-sectional area of the communicating bore along the working length thereof does not exceed 7 mm$^2$. Advantageously, the transverse cross-section area of the communicating bore along the working length thereof lies in the range of 0.0079 mm$^2$ to 3.142 mm$^2$.

Ideally, the transverse cross-section area of the communicating bore along the working length thereof lies in the range of 0.0079 mm$^2$ to 1.78 mm$^2$. Preferably, the transverse cross-sectional area of the communicating bore along the working length thereof does not exceed 1.35 mm$^2$. Ideally, the transverse cross-sectional area of the communicating bore along the working length thereof is approximately 0.2 mm$^2$.

In another aspect of the invention the maximum transverse cross-sectional dimension of the communicating bore along the working length thereof does not exceed 5 mm. Preferably, the maximum transverse cross-sectional dimension of the communicating bore along the working length thereof does not exceed 3 mm. Advantageously, the maximum transverse cross-sectional dimension of the communicating bore along the working length thereof lies in the range of 0.1 mm to 2 mm. Ideally, the maximum transverse cross-sectional dimension of the communicating bore along the working length thereof lies in the range of 0.1 mm to 1.5 mm.

Preferably, the maximum transverse cross-sectional dimension of the communicating bore along the working length thereof does not exceed 1.31 mm. Ideally, the maximum transverse cross-sectional area of the communicating bore along the working length thereof is approximately 0.5 mm.

In another aspect of the invention the communicating bore along the working length thereof is of circular transverse cross-section.

In another aspect of the invention the communicating bore along the working length thereof comprises a capillary bore.

In a further aspect of the invention the communicating bore is of constant transverse cross-sectional area along the working length thereof.

In an alternative aspect of the invention the transverse cross-sectional area along the working length of the communicating bore varies.

In one aspect of the invention the transverse cross-sectional area along the working length of the communicating bore varies in at least one step change.

In another aspect of the invention the transverse cross-sectional area of the communicating bore is smallest adjacent the gas chamber.

In a further aspect of the invention the gas chamber comprises a fixed volume chamber.

In a further aspect of the invention the volume of the gas chamber does not exceed 10 mm$^3$. Preferably, the volume of the gas chamber does not exceed 5 mm$^3$. Advantageously, the volume of the gas chamber does not exceed 1 mm$^3$. Preferably, the volume of the gas chamber lies in the range of 0.05 mm$^3$ to 0.5 mm$^3$. Ideally, the volume of the gas chamber is approximately 0.1 mm$^3$.

Preferably, the gas chamber comprises a sealed chamber.

In one aspect of the invention the apparatus comprises a housing defining the gas chamber.

Preferably, the pressure sensor is located in the housing with the pressure sensor interface communicating with the gas chamber. Advantageously, the communicating bore extends from the gas chamber through the housing.

In another aspect of the invention the communicating bore comprises an elongated bore extending through an elongated conduit, the conduit extending between a first end communicating with the gas chamber and a second end configured for extending into a vessel in which the liquid, the pressure of which is to be monitored is contained. Preferably, the conduit extends from the housing, and the second end of the conduit is adapted to terminate in the vessel in which the pressure of the liquid therein is to be monitored.

In one aspect of the invention the pressure monitoring apparatus is configured for coupling to a catheter.

In another aspect of the invention the pressure monitoring apparatus is configured for coupling to a catheter adjacent a distal end thereof.

In a further aspect of the invention the housing is configured for mounting on the catheter.

Preferably, the housing is configured for mounting in alignment with the catheter.

In one aspect of the invention the pressure monitoring apparatus is configured for releasable coupling to the catheter.

In another aspect of the invention the communicating bore is configured to extend from the gas chamber along a portion of the catheter and to terminate adjacent an outer surface of the catheter. Preferably, the communicating bore is configured to extend longitudinally along the catheter.

In another aspect of the invention the communicating bore is configured to extend through the catheter.

In another aspect of the invention the communicating bore is configured to extend externally of the catheter adjacent thereto.

In a further aspect of the invention the pressure monitoring apparatus is configured for mounting on an endoscope for monitoring the pressure in a vessel within which the endoscope is located.

Preferably, the pressure monitoring apparatus is configured for releasable mounting on the endoscope.

In one aspect of the invention the pressure monitoring apparatus is configured for mounting adjacent a distal end of the endoscope. Preferably, a securing means is provided for securing the housing to the endoscope.

In one aspect of the invention the pressure monitoring apparatus is configured for mounting an external surface of the endoscope. Preferably, the securing means comprises a collar configured to extend around the endoscope. Advantageously, the securing means comprises a strap.

In an alternative aspect of the invention the pressure monitoring apparatus is configured for mounting in a bore of the endoscope. Preferably, the communicating bore extends to the distal end of the endoscope. Advantageously, the second end of the conduit defining the communicating bore is configured for receiving an extension conduit thereon. Preferably, the second end of the conduit defining the communicating bore is configured for releasably receiving the extension conduit.

In one aspect of the invention the extension conduit is configured for securing to an external surface of the endoscope. Preferably, the extension conduit comprises a disposable conduit.

In one aspect of the invention the gas comprises a non-electrically conductive gas. In another aspect of the invention the gas comprises air.

In one aspect of the invention the communicating bore extends from the gas chamber along a portion of the catheter and terminates adjacent an outer surface of the catheter. Preferably, the communicating bore extends longitudinally along the catheter.

In one aspect of the invention the communicating bore extends through the catheter.

In another aspect of the invention the communicating bore comprises an elongated bore extending through an elongated conduit, the conduit extending between a first end communicating with the gas chamber and a second end configured for extending into a vessel in which the liquid, the pressure of which is to be monitored is contained.

In one aspect of the invention the conduit extends externally along the catheter.

In another aspect of the invention the conduit extends internally in the catheter, and the second end of the catheter communicates with an opening in the external surface of the catheter.

In a further aspect of the invention the conduit is sealably engaged in a lumen of the catheter, and the second end of the conduit communicates with the lumen.

Preferably, the conduit extends into the catheter from the distal end thereof.

In another aspect of the invention the gas chamber is formed in the catheter.

Preferably, the gas chamber is formed in the catheter adjacent the distal end thereof.

In another aspect of the invention the pressure monitoring apparatus comprises a housing, the housing defining the gas chamber. Preferably, the housing is mounted on the catheter. Advantageously, the housing defines the gas chamber with the catheter.

In one aspect of the invention the housing is mounted on the catheter adjacent the distal end thereof.

Preferably, the housing is sealably secured to the catheter. Advantageously, the communicating bore extends through the housing.

In one aspect of the invention the housing is of external transverse cross-section substantially similar to the external transverse cross-section of the catheter.

Preferably, the housing is aligned with the catheter. Advantageously, the housing is releasably secured to the catheter.

In one aspect of the invention a balloon is mounted on the catheter, and the communicating bore communicates with the balloon.

Preferably, the communicating bore terminates within the balloon.

In one aspect of the invention the balloon extends around the catheter and defines with the catheter an annular hollow interior region.

Preferably, the balloon is located adjacent the distal end of the catheter.

The advantages of the invention are many. A particularly important advantage of the invention is that the pressure monitoring apparatus permits monitoring of the pressure of a liquid which may be electrically conductive by an electrical, an electronic or a solid state pressure monitoring means which must be maintained in a non-electrically conducting environment. Another advantage of the invention is that by virtue of the fact that electrical, electronic and solid state pressure sensors are relatively accurate, and produce a signal indicative of the pressure being monitored substantially instantaneously without any time delays, the pressure monitoring apparatus allows the pressure of a liquid to be monitored with a high degree of accuracy and substantially instantaneously without any time delays.

A particularly important advantage is achieved by the invention when the pressure monitoring apparatus is used in conjunction with a catheter, and in particular a balloon catheter where the balloon catheter is of the type which requires inflating of the balloon by an electrically conductive liquid. Since the pressure sensor is isolated from the liquid by gas, which typically is air, there is no danger of the electrically conductive liquid coming in contact with the pressure sensor. Additionally, the advantage of being able to provide a substantially instantaneous value of the pressure of the inflating liquid in the balloon of a balloon catheter of relatively high accuracy is a particularly important advantage when a balloon is being inflated in a vessel, lumen or cavity in the body of a human or animal subject for dilating the vessel. In such cases it is essential that the pressure of the inflating liquid within the balloon as the balloon is being inflated can be substantially instantaneously provided, in order to avoid the risk of damage, for example, rupturing of the vessel, lumen or cavity.

Figure 4:
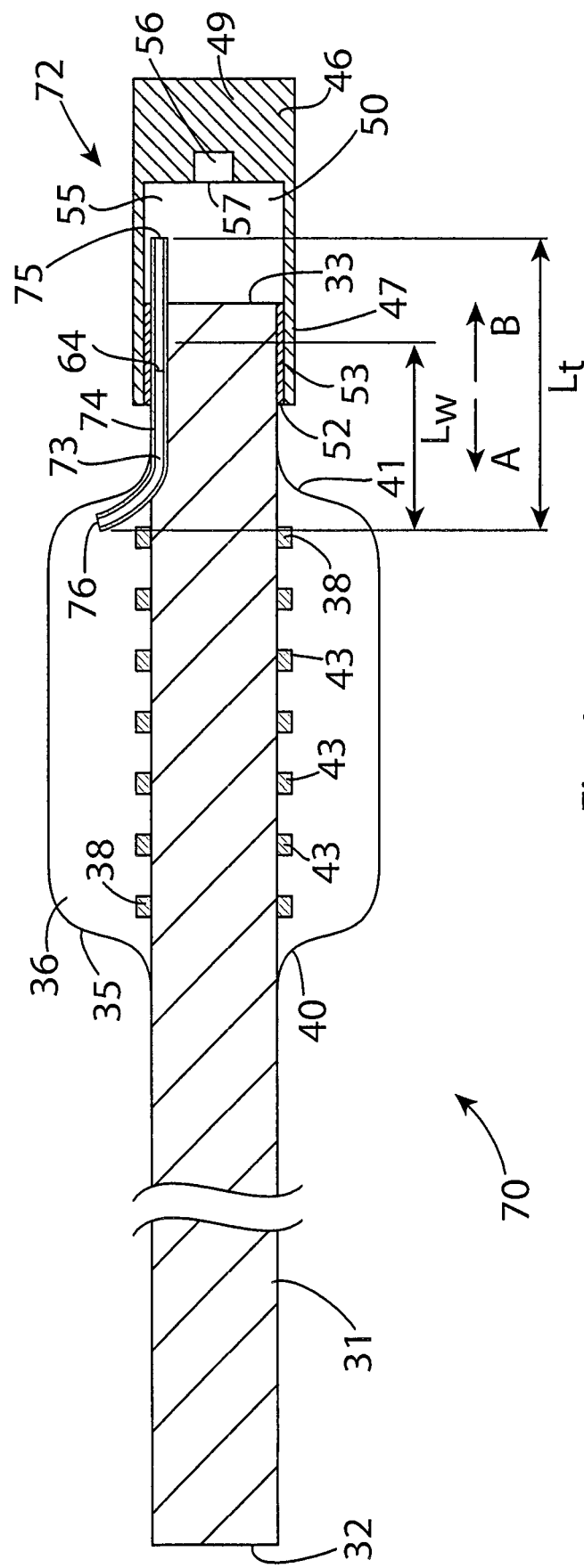
Figure 7:
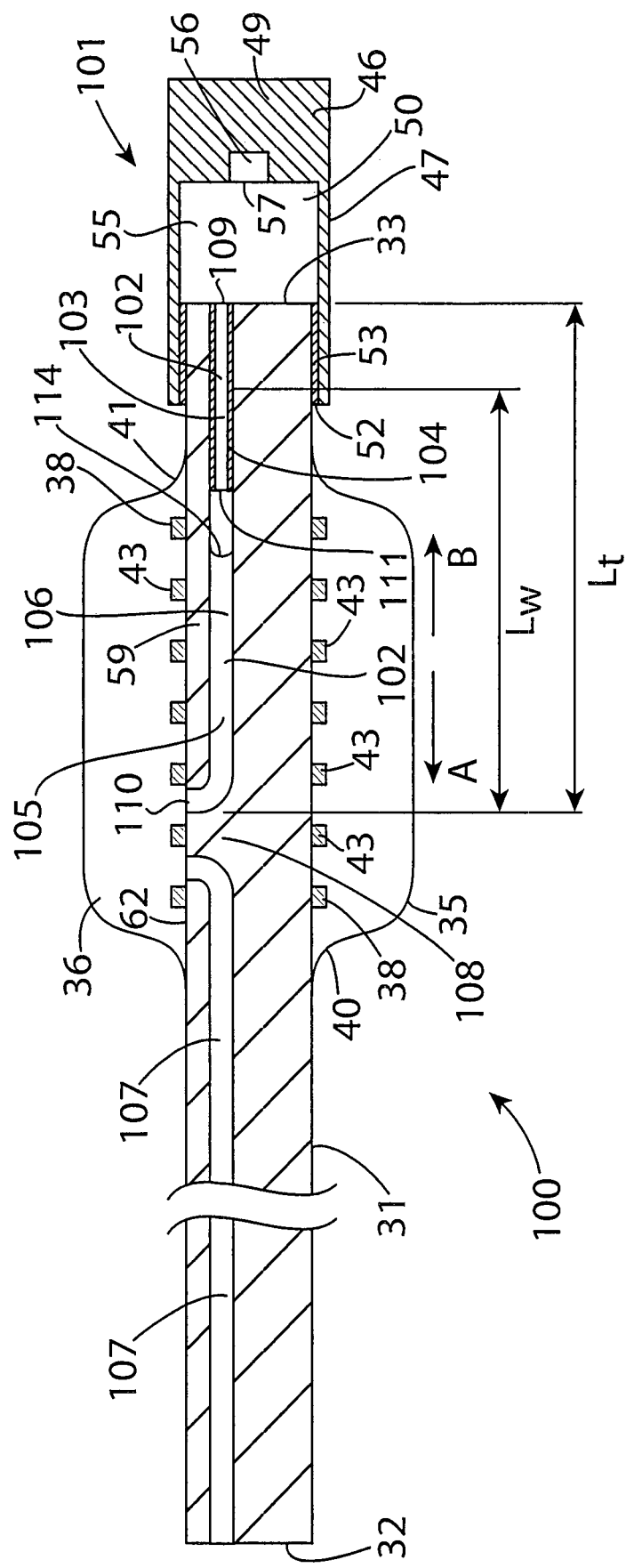

The invention will be more clearly understood from the following description of some preferred embodiments thereof, which are given by way of example only, with reference to the accompanying drawings, in which:

FIG. 1 is a diagrammatic cross-sectional side elevational view (not to scale) of a pressure monitoring apparatus according to the invention for monitoring pressure in a liquid, FIG. 2 is a view (not to scale) similar to FIG. 1 of the pressure monitoring apparatus of FIG. 1 in use monitoring pressure in a liquid, FIG. 3 is a cross-sectional side elevational view (not to scale) of a catheter according to the invention in this case a balloon catheter comprising a pressure monitoring apparatus also according to the invention, FIG. 4 is a view (not to scale) similar to FIG. 3 of a catheter in this case also a balloon catheter according to another embodiment of the invention comprising a pressure monitoring apparatus also according to the invention, FIG. 5 is a cross-sectional side elevational view (not to scale) of an endoscope according to the invention comprising a pressure monitoring apparatus also according to the invention mounted thereon, FIG. 6 is a perspective view (not to scale) of a portion of the endoscope of FIG. 5 with the pressure monitoring apparatus of FIG. 6 mounted thereon, FIG. 7 is a view (not to scale) similar to FIG. 3 of a catheter, in this case also a balloon catheter according to another embodiment of the invention comprising a pressure monitoring apparatus also according to the invention, FIG. 8 is a side elevational view (not to scale) of a distal portion of an endoscope according to another embodiment of the invention comprising a pressure monitoring apparatus also according to the invention, and FIG. 9 is a cross-sectional side elevational view (not to scale) of the portion of the endoscope and the pressure monitoring apparatus of FIG. 8.

Referring to the drawings and initially to FIGS. 1 and 2, there is illustrated a pressure monitoring apparatus according to the invention, indicated generally by the reference numeral 1, for monitoring pressure in a liquid 4. In this embodiment of the invention the liquid 4 is contained in a vessel 2, which may be any type of vessel, for example, an expandable vessel, a rigid vessel or the like. The vessel 2 could also be a vessel in a human or animal subject in which it is desired to monitor liquid pressure, or the vessel 2 may, for example, be a balloon of a balloon catheter where the balloon is being inflated with an electrically conductive liquid, as will be described below with reference to the embodiments of the invention which are described with reference to FIGS. 3 and 4. However, for the purpose of describing the pressure monitoring apparatus 1 according to the invention, the vessel 2 may be any vessel in which the pressure of a liquid 4 therein is to be monitored.

The pressure monitoring apparatus 1 in this embodiment of the invention comprises a housing 3 having a hollow interior region 5, which forms an airtight gas chamber 6 containing a gas, in this embodiment of the invention air. A pressure sensor 8, which in this embodiment of the invention comprises a piezoresistive sensor, is located within the housing 3. The pressure sensor 8 comprises a pressure sensing interface 10, and the pressure sensor 8 is located in the housing 3 with the pressure sensing interface 10 communicating with the air in the gas chamber 6 for monitoring the pressure of the air therein. In this embodiment of the invention the volume of the gas chamber 6 is approximately 0.1 mm$^3$.

An elongated conduit 12 extending between a first end 14 and a second end 15 defines an elongated communicating bore 16 extending from the first end 14 to the second end 15 for communicating the gas chamber 6 with the liquid 4 in the vessel 2. The conduit 12 extends sealably through the housing 3 with the first end 14 terminating in the gas chamber 6 for communicating the communicating bore 16 with the gas chamber 6 through the first end 14 of the conduit 12. The conduit 12 extends sealably into the vessel 2 with the second end 15 of the conduit 12 located in the vessel 2 and with the communicating bore 16 communicating with the liquid 4 in the vessel 2 through the second end 15 of the conduit 12. The communicating bore 16 is of circular transverse cross-section and is of constant diameter over the total length $L_t$ of the conduit 12 from the first end 14 to the second end 15. In this embodiment of the invention the diameter of the communicating bore 16 is approximately 0.5 mm, and the total length $L_t$ of the conduit 12 between the first end 14 and the second end 15 is approximately 30 mm.

The conduit 12 is of a material, which is a copolymer of polyester and polyamide, which defines an inner surface 18, which in turn defines the communicating bore 16. The inner surface 18 of the conduit 12 which defines the communicating bore 16 is such that in combination with the transverse cross-sectional area of the communicating bore results in the formation of a liquid/gas interface meniscus 20 which extends across the communicating bore 16, and the periphery of the liquid/gas interface meniscus 20 extends completely around and engages the inner surface 18 of the conduit 12 defining the communicating bore 16. Additionally, as a result of the transverse cross-sectional area of the communicating bore 16, and the inner surface 18 of the conduit 12 which defines the communicating bore 16, the surface tension induced in the liquid/gas interface meniscus 20 is such as to prevent gas from either penetrating through the liquid/gas interface meniscus, or passing in the direction of the arrow A past the liquid/gas interface meniscus 20. Additionally, the surface tension induced in the liquid/gas interface meniscus 20 is such as to prevent liquid from either penetrating through the liquid/gas interface meniscus 20 or passing in the direction of the arrow B past the liquid/gas interface meniscus 20. Accordingly, the liquid/gas interface meniscus 20 acts as a barrier between the liquid on the one hand, and the gas on the other hand on the respective opposite sides of the liquid/gas interface meniscus 20 passing through or across the liquid/gas interface meniscus 20.

Accordingly, as the pressure of the liquid in the vessel 2 increases, the liquid/gas interface meniscus 20 progressively travels along the communicating bore 16 of the conduit 12 in the direction of the arrow B, thereby progressively increasing the pressure of the air in the gas chamber 6. Reduction in the pressure in the liquid in the vessel 2 results in the liquid/gas interface meniscus 20 travelling along the communicating bore 16 of the conduit 12 in the direction of the arrow A thereby correspondingly reducing the pressure of the air in the gas chamber 6. The pressure of the air in the gas chamber 6, which is similar to the pressure in the liquid in the vessel 2, is monitored by the pressure sensor 8, which in turn produces an accurate reading of the pressure of the liquid in the vessel 2 substantially instantaneously.

In order to avoid any danger of the liquid/gas interface meniscus 20 travelling the full length $L_t$ of the communicating bore 16 from the second end 15 to the first end 14, which would thereby allow liquid to flow through the communicating conduit 12 into the gas chamber 6, it is essential that the total length $L_t$ of the communicating bore 16 should be such that the travel of the liquid/gas interface meniscus 20 along the communicating bore 16 should be contained within a working length $L_w$ of the communicating bore 16 as the pressure in the liquid varies from the minimum pressure, for example, atmospheric pressure to the maximum pressure which would be reached by the liquid in the vessel 2. The working length $L_w$ of the communicating bore 16 should therefore be less than the total length $L_t$ of the conduit 12, and in turn the total length of the communicating bore 16. Typically, the working length $L_w$ of the communicating bore 16 would be not more than eighty percent of the total length $L_t$ of the communicating bore 16, and ideally, should be approximately fifty percent of the total length $L_t$ of the communicating bore 16.

The total length $L_t$ of the communicating bore 16 to accommodate a known maximum pressure to which the liquid in the vessel 2 may be pressurised can be readily computed as follows. The volume of the air being compressed as the pressure of the liquid in the vessel 2 increases is the total volume of air in the gas chamber 6 and the total volume of air in the communicating bore 16. Accordingly, based on the Combined Gas Law if:

P1=starting pressure of the liquid in the vessel 2, typically atmospheric pressure, P2=maximum pressure which would be reached by the liquid in the vessel 2,
Va$^1$=total volume of air in the gas chamber 6 and the communicating bore 16 at pressure P1, which typically would be atmospheric pressure,
Va$^2$=volume to which the total volume of air would be compressed when the pressure in the liquid in the vessel 2 has reached the maximum pressure P2,
T1=starting temperature,
T2=temperature when the pressure of the liquid in the vessel 2 has reached the maximum pressure P2,
The Combined Gas Law provides $$\frac{P1 \cdot Va^1}{T1} = \frac{P2 \cdot Va^2}{T2} \quad (1)$$

Assuming no significant temperature change occurs as the pressure of the liquid in the vessel 2 increases from the starting pressure P1 to the maximum pressure P2 equation (1) can be rewritten as (Boyles Law) as:

$$Va^2 = \frac{P1 \cdot Va^1}{P2} \quad (2)$$

By subtracting the volume of air Va$^t$ after compression from the initial volume of air Va$^1$, the change in the volume of air ($\Delta V$) as the pressure in the liquid in the vessel 2 goes from P1 to the maximum pressure P2 is determined as follows:

$$\Delta V = Va^1 - \frac{P1 \cdot Va^1}{P2} \quad (3)$$

The working length of the communicating bore 16 required to contain the liquid/gas interface meniscus 20 within the communicating bore 16 to accommodate a maximum pressure of the liquid in the vessel 2 of pressure P2 can be calculated as follows if:
r=the radius of the communicating bore 16,
$L_w$=the working length of the communicating bore 16,
If the change in volume $\Delta V$ is to be taken up entirely within the working length $L_w$ of the communicating bore 16, the working length $L_w$ of the communicating bore 16 must be at least $$L_w = \frac{\Delta V}{\pi r^2} \quad (4)$$

Substituting for $\Delta V$ in equation (4) from equation (3) the working length $L_w$ of the communicating bore 16 is as follows:

$$L_w = \frac{Va^1}{\pi r^2}\left(1 - \frac{P1}{P2}\right) \quad (5)$$

The length $L_w$ computed from equation (5) is essentially the working length over which the liquid/gas interface meniscus 20 would travel in the communicating bore 16 as the pressure of the liquid in the vessel 2 varied from the starting pressure P1, typically atmospheric pressure to the maximum pressure. Thus, in order to ensure that the liquid/gas interface meniscus 20 does not extend beyond the working length $L_w$ of the communicating bore 16 as the pressure of the liquid rises, the total length $L_t$ of the communicating bore 16 in practice would be made longer than the computed working length $L_w$ of the communicating bore 16, and as discussed above, would typically be selected to be approximately twice as long as the computed working length $L_w$ of the communicating bore 16.

As can be seen the working length $L_w$ of the communicating bore 16 of the conduit 12 is proportional to the total volume of the communicating bore 16 and the gas chamber 6. Thus, by reducing the volume of the gas chamber 6, the required working length $L_w$ of the communicating bore 16 can be reduced.

Accordingly, since the liquid/gas interface meniscus 20 is impenetrable by air, and since air is not permitted to pass the liquid/gas interface meniscus 20 and furthermore, since the liquid/gas interface meniscus 20 is also impenetrable by liquid and since liquid is not permitted to pass the liquid/gas interface meniscus 20, there is no danger of liquid entering the gas chamber 6 provided that the working length $L_w$ of the communicating bore 16 is sufficiently long to accommodate the pressure range up to the maximum pressure to which the liquid in the vessel 2 is likely to reach, and furthermore, that the total length $L_t$ of the communicating bore 16, is greater than the required working length $L_w$ of the communicating bore 16.

In FIG. 1 initially the pressure of the air in the gas chamber 6 and the pressure in the liquid 4 in the vessel 2 is atmospheric pressure. As the pressure of the liquid 4 in the vessel 2 commences to increase, the liquid commences to travel into the communicating bore 16 of the conduit 12 from the second end 15, thereby forming the liquid/gas interface meniscus 20 in the communicating bore 16, see FIG. 2. The travel of the liquid/gas interface meniscus 20 along the communicating bore 16 of the conduit 12 correspondingly increases the pressure of the air in the gas chamber 6, which is monitored by the pressure sensor 8, which gives an immediate and true reading of the pressure of the liquid in the vessel 2.

It has been found that for a saline solution and air which produces a saline solution/air interface meniscus by providing the communicating bore 16 to be of diameter in the range of 0.1 mm to 2 mm, and preferably, of diameter of 0.5 mm, the surface tension induced in the saline solution/air interface meniscus 20 is such as to prevent the air penetrating or passing by the saline solution/air interface meniscus 20 and also to prevent the liquid penetrating or passing by the saline solution/air interface meniscus 20. Accordingly, there is no danger of the air exiting the gas chamber 6 through the communicating bore 16 of the conduit 12, and in turn, there is no danger of the saline solution from the vessel 2 penetrating into the gas chamber 6, provided that the working length $L_w$ of the communicating bore 16 of the conduit 12 is sufficient to accommodate the pressure range up to the maximum pressure which would be reached by the saline solution in the vessel 2, and that the total length $L_t$ of the communicating bore 16 is greater than the working length $L_w$.

In use, when it is desired to monitor pressure of a liquid in a vessel, such as the vessel 2, the second end 15 of the communicating bore 16 of the conduit 12 is initially exposed to air at atmospheric pressure, so that the pressure of the air in the gas chamber 6 is at atmospheric pressure. The second end 15 of the conduit 12 is then immersed in the liquid 4 in the vessel 2, the pressure of which is to be monitored. As the pressure of the liquid 4 in the vessel 2 increases, the liquid/gas interface meniscus 20 travels in the direction of the arrow B along the communicating bore 16 of the conduit 12, thereby correspondingly increasing the pressure of the air in the gas chamber 6 which is detected by the pressure sensor 8, thereby giving a substantially instant and accurate reading of the pressure of the liquid in the vessel 2.

When the pressure in the liquid 4 in the vessel 2 reduces to atmosphere, the liquid/air interface meniscus 20 travels back to the second end 15 of the communicating bore 16 of the conduit 12 as illustrated in FIG. 1.

Referring now to FIG. 3, there is illustrated a catheter also according to the invention, which in this embodiment of the invention comprises a balloon catheter indicated generally by the reference numeral 30. The balloon catheter 30 comprises an elongated catheter 31 extending between a proximal end 32 and a distal end 33. A balloon 35 is located on the catheter 31 adjacent the distal end 33, with the catheter 31 extending through the balloon 35 to define with the balloon 35 an annular hollow interior region 36.

In this embodiment of the invention the balloon catheter 30 is of the type which is suitable for carrying out impedance planimetry measurements of the type described in PCT Specification No. WO 2009/001328. A pair of spaced apart stimulating electrodes 38 are located on the catheter 31 within the balloon 35 adjacent respective proximal and distal ends 40 and 41 of the balloon 35, and a plurality of spaced apart sensing electrodes 43 are located on the catheter 31 between and spaced apart from the stimulating electrodes 38. By inflating the balloon 35 with an electrically conductive medium, typically, a saline solution, and by applying a stimulating constant current signal to the stimulating electrodes 38, signals read from the sensing electrodes 43 are indicative of the diameter of the balloon adjacent the respective sensing electrodes 43. The use of such balloon catheters for determining the volume and cross-sectional area of a vessel, lumen or cavity in the body of a human or animal subject within which the balloon 35 is located and inflate with a saline solution will be well known to those skilled in the art, and as discussed above, is described in PCT Specification No. WO 2009/001328.

A pressure monitoring apparatus also according to the invention and indicated generally by the reference numeral 45, is located adjacent the distal end 33 of the catheter 31, and is configured for monitoring the pressures of the saline solution in the hollow interior region 36 of the balloon 35. The pressure monitoring apparatus 45 comprises a housing 46 of cylindrical construction having a cylindrical side wall 47 closed at one end by an end cap 49, and defining with the end cap 49 a hollow interior region 50. The side wall 47 adjacent the opposite end to that of the end cap 49 defines an open mouth 52 to the hollow interior region 50. The housing 46 is mounted on the distal end 33 of the catheter 31 by engaging the distal end 33 of the catheter 31 in the open mouth 52 of the housing 46. A sealant bonding agent 53 around the catheter 31 adjacent the distal end 33 thereof sealably secures the side wall 47 of the housing 46 adjacent the open mouth 52 to the catheter 31 adjacent the distal end 33 thereof, so that the housing 46 defines with the distal end 33 of the catheter 31 a sealed gas chamber 55.

A pressure sensor 56 similar to the pressure sensor 8 of the pressure monitoring apparatus 1 is located in the end cap 49 of the housing 46, and a pressure sensing interface 57 of the pressure sensor 56 communicates with the gas chamber 55. Alternatively, the pressure sensor 56 may be located in the catheter 31 adjacent the distal end 33 with the pressure sensing interface 57 thereof communicating with the gas chamber 55.

An elongated communicating bore 58 extends through a distal portion 59 of the catheter 31 from the distal end 33 of the catheter 31, and terminates in an outer surface 62 of the catheter 31 within the balloon 35. The communicating bore 58 communicates with the gas chamber 55 through a first end 60 adjacent the distal end 33 of the catheter 31 and communicates with the hollow interior region 36 of the balloon 35 through a second end 61 adjacent the surface 62 of the catheter 31 for in turn communicating the hollow interior region 36 of the balloon 35 with the gas chamber 55 in the housing 46. Initially the gas chamber 55 and the communicating bore 58 over its total length $L_t$ from the first end 60 to the second end 61 is filled with air, typically, at atmospheric pressure.

As saline solution is delivered into the hollow interior region 36 of the balloon 35 and the pressure of the saline solution in the balloon 35 commences to increase, a saline solution/air interface meniscus 64 is formed in the communicating bore 56 adjacent the second end 61. As the pressure of the saline solution in the balloon 35 increases, the saline solution/air interface meniscus 64 commences to travel along the communicating bore 56 in the direction of the arrow B from the second end 61 towards the first end 60. As the saline solution/air interface meniscus 64 travels in the direction of the arrow B along the communicating bore 58, the pressure of the air in the gas chamber 55 increases to equal the pressure of the saline solution in the hollow interior region 36 of the balloon 35. Thus, the pressure of the air in the gas chamber 55 monitored by the pressure sensor 56 is identical to the pressure of the saline solution in the hollow interior region 36 of the balloon 35.

A communicating means, namely, electrically conductive wires (not shown) extend from the pressure sensor 56 through a suitable longitudinal lumen (also not shown) extending through the catheter 31 to the proximal end 32 of the catheter 31 for providing signals indicative of the pressure monitored by the pressure sensor 56. Alternatively, the communicating means may be provided by a radio transmitter located in the end cap 49 of the housing 46, which would transmit signals indicative of the pressure monitored by the pressure sensor 56. Such means of communicating signals from the pressure sensor 56 will be well known to those skilled in the art. Additionally, electrically conductive wires (not shown) are provided extending through a lumen (not shown) in the catheter 31 from the proximal end 32 thereof to the stimulating electrodes 38 and the sensing electrodes 43 for applying the electrical stimulating current to the stimulating electrodes 38 and for reading signals from the sensing electrodes 43. This will be well known to those skilled in the art, and is described in PCT Specification No. WO 2009/001328. Additionally, a saline solution delivery lumen (not shown) is also provided extending through the catheter 31 from the proximal end 32 which terminate in the balloon 35 for inflating the balloon 35 with the saline solution.

A control circuit (not shown) typically comprising a microprocessor controls the operation of the balloon catheter 30, and controls the delivery of the stimulating current to the stimulating electrodes 38, and reads signals from the sensing electrodes 43 for determining the transverse cross-sectional area of the balloon 35 adjacent the respective sensing electrodes 43, and for in turn determining the volume of the balloon 35. The microprocessor also reads signals from the pressure sensor 56 for monitoring the pressure of the saline solution in the balloon 35 as the balloon 35 is being inflated.

A visual display unit (not shown) is also provided for displaying a two-dimensional and/or a three-dimensional image of the balloon and for displaying the values of the transverse cross-sectional areas of the balloon adjacent the respective sensing electrodes 43 and the volume of the balloon, as well as the pressure of the saline solution in the balloon 35 as the balloon 35 is being inflated. The control of such a balloon catheter and the display of relevant images of the balloon and relevant data read from signals from sensing electrodes and a pressure sensor monitoring the pressure of the saline solution in the balloon is disclosed in PCT Specification No. WO 2009/001328.

As already described with reference to the pressure monitoring apparatus 1, which is described with reference to FIGS. 1 and 2, the total length $L_t$ of the communicating bore 58 must be greater than the working length $L_w$ of the communicating bore 58, and as described with reference to FIGS. 1 and 2, the working length $L_w$ of the communicating bore 58 must be of length sufficient to contain the travel of the saline solution/air interface meniscus 64 along the communicating bore 58 up to the maximum pressure of the saline solution with which the balloon 35 is to be inflated.

In this embodiment of the invention the volume of the gas chamber 55 is 0.1 mm$^3$ and the total length $L_t$ of the communicating bore 58 from the first end 60 to the second end 61 is 30 mm. The communicating bore 58 is of circular transverse cross-section of constant diameter of 0.5 mm over its entire length.

In use, when it is desired to determine the volume and/or transverse cross-sectional area of a vessel, lumen or cavity in a human or animal subject, or when it is desired to determine the compliance of a vessel, lumen, cavity or sphincter in a human or animal subject, or indeed when it is desired to dilate a vessel, lumen, cavity or sphincter in a human or animal subject, the balloon catheter 30 is appropriately inserted into the human or animal subject with the balloon 35 located in the vessel, lumen, cavity or sphincter as the case may be. The balloon 35 is then inflated with the saline solution, and as the balloon 35 is being inflated with the saline solution a constant electrical current is applied to the stimulating electrodes 38. Signals from the sensing electrodes 43 are monitored and the transverse cross-sectional area and/or the volume of the vessel, lumen, cavity or sphincter is determined from signals read from the sensing electrodes 43. The pressure of the saline solution in the balloon 35 is read from signals from the pressure sensor 56.

By virtue of the fact that as the pressure of the saline solution in the balloon 35 increases the saline solution/air interface meniscus 64 travels in the direction of the arrow B along the communicating bore 58 thereby compressing the air in the gas chamber 55 to a pressure similar to the pressure of the saline solution in the balloon 35, the signals read from the pressure sensor 56 produce an almost instantaneous reading of the pressure of the saline solution in the balloon 35.

Referring now to FIG. 4 there is illustrated a balloon catheter according to another embodiment of the invention, indicated generally by the reference numeral 70, to which a pressure monitoring apparatus also according to the invention, and indicated generally by the reference numeral 72 is mounted for monitoring the pressure of the liquid in the balloon 35 of the balloon catheter 70. The balloon catheter 70 and the pressure monitoring apparatus 72 are substantially similar to the balloon catheter 30 and the pressure monitoring apparatus 45 of FIG. 3, and similar components are identified by the same reference numerals.

The main difference between the balloon catheter 70 and the pressure monitoring apparatus 72 and the balloon catheter 30 and the pressure monitoring apparatus 45 is that in this embodiment of the invention the elongated communicating bore which communicates the gas chamber 55 with the hollow interior region 36 of the balloon 35 is formed by an elongated communicating bore 73 extending through an elongated conduit 74. The conduit 74 extends between a first end 75 and a second end 76, and extends longitudinally along and exteriorly of the catheter 31 but adjacent thereto. The first end 75 of the conduit 74 extends into the gas chamber 55 with the first end of the communicating bore 73 communicating with the gas chamber 55. The conduit 74 extends into the gas chamber 55 between the catheter 31 and the cylindrical side wall 47 of the housing 46, and is sealably secured between the catheter 31 and the side wall 47 of the housing 46 by the adhesive bonding agent 53 to ensure complete sealing of the gas chamber 55. The conduit 74 extends into the hollow interior region 36 of the balloon 35 between the catheter 31 and the portion of the balloon 35 secured to the catheter 31, and is sealably secured between the catheter 31 and the balloon 35 in order to ensure a watertight seal between the balloon 35, the catheter 31 and the conduit 74.

In this embodiment of the invention the conduit 74 is of similar material to that of the conduit 12, and the communicating bore 73 of the conduit 74 is of similar diameter to the diameter of the communicating bore 16 of the conduit 12, and the inside surface of the conduit 73 defining the communicating bore 73 is substantially similar to the inside surface 18 of the conduit 12 defining the communicating bore 16. The total length $L_t$ of the conduit 74 and in turn the communicating bore 73 from the first end 75 to the second end 76 in this embodiment of the invention is 20 mm, and the working length $L_w$ approximately 10 mm, which is sufficient to contain the saline solution/air interface meniscus 64 over the maximum range of operating pressures of the saline solution within the balloon 35.

The volume of the gas chamber 55 in this embodiment of the invention is similar to the volume of the gas chamber 55 of the balloon catheter 30.

Otherwise the balloon catheter 70 and the pressure monitoring apparatus 72 and their use are similar to the balloon catheter 30 and the pressure monitoring apparatus 45 described with reference to FIG. 3.

Referring now to FIGS. 5 and 6, there is illustrated an endoscope also according to the invention, and indicated generally by the reference numeral 80, onto which a pressure monitoring apparatus also according to the invention, and indicated generally by the reference numeral 81, is releasably secured adjacent a distal end 82 of the endoscope 80 for monitoring the pressure of a liquid in a vessel, lumen or cavity in a human or animal subject in which the distal end 82 of the endoscope is located. Such endoscopes as the endoscope 80 will be well known to those skilled in the art.

The pressure monitoring apparatus 81 comprises a housing 83 which is releasably secured to the endoscope 80 adjacent the distal end 82 by a collar 84 extending around the endoscope 80 adjacent the distal end 82 thereof. The housing 83 defines an airtight gas chamber 85. A pressure sensor 86 is located in the housing 83, with a pressure sensing interface 87 thereof communicating with the gas chamber 85 for monitoring the pressure in the gas chamber 85. The pressure sensor 86 is similar to the pressure sensor 8 of the pressure monitoring apparatus 1 described with reference to FIGS. 1 and 2.

An elongated conduit 88 substantially similar to the conduit 12 of the pressure monitoring apparatus 1 described with reference to FIGS. 1 and 2 extends between a first end 90 and a second end 91 and defines an elongated communicating bore 92 extending therethrough from the first end 90 to the second end 91. The conduit 88 extends sealably through the housing 83 with the first end 90 terminating in the gas chamber 85 so that the communicating bore 92 of the conduit 88 communicates the gas chamber 85 through the second end 91 of the communicating bore 92 externally of the gas chamber 85. Thus, when the distal end 82 of the endoscope 80 is located in a vessel, lumen or cavity in a human or animal subject, the pressure of liquid in the vessel, lumen or cavity can be monitored by the pressure monitoring apparatus 81, once the second end 91 of the communicating bore 92 communicates with the liquid.

In use, when the distal end 82 of the endoscope 80 is located in a vessel, lumen or cavity in a human or animal subject, and the second end 91 of the conduit 88 is located in the vessel, lumen or cavity the pressure of liquid in the vessel may be monitored by the pressure monitoring apparatus 81. Initially, prior to inserting the endoscope 80 into the subject, the second end 91 of the conduit 88 is exposed to air at atmospheric pressure such that the air in the gas chamber 85 and the communicating bore 92 are at atmospheric pressure. When the distal end 82 of the endoscope 80 is located in the vessel, lumen or cavity of the subject with the second end 91 of the conduit 88 located in the vessel, lumen or cavity, liquid in the vessel, lumen or cavity communicates with the communicating bore 92. The liquid in the vessel, lumen or cavity depending on the pressure thereof forms a liquid/gas interface meniscus 93 similar to the liquid/gas interface meniscus 20 formed in the communicating bore 16 of the conduit 12 of the pressure monitoring apparatus 1. Depending on the pressure of the liquid in the vessel, lumen or cavity the liquid/gas interface meniscus 93 moves along the communicating bore 92 from the second end 91 towards the first end 90 within the working length $L_W$ of the communicating bore 92. This as already described with reference to the pressure monitoring apparatus 1 described with reference to FIGS. 1 and 2 results in compression of the air in the communicating bore 92 and in the gas chamber 85, which in turn results in an increase in pressure of the air in the gas chamber 85. The pressure of the air in the gas chamber 85 is monitored by the pressure sensor 86, and signals read from the pressure sensor 86 are indicative of the pressure of the liquid in the vessel, lumen or cavity in the human or animal subject.

Referring now to FIG. 7, there is illustrated a balloon catheter according to another embodiment of the invention indicated generally by the reference numeral 100 which also comprises a pressure monitoring apparatus, also according to the invention and indicated generally by the reference numeral 101. The balloon catheter 100 is substantially similar to the balloon catheter 30 described with reference to FIG. 3, and similar components are identified by the same reference numerals. The pressure monitoring apparatus 101 is also substantially similar to the pressure monitoring apparatus 45 of the balloon catheter 30 of FIG. 3, and similar components are identified by the same reference numerals. The main difference between the balloon catheter 100 and the apparatus 101 lies substantially in the balloon catheter 101.

In this embodiment of the invention the communicating bore 102 is formed in series in part by a first communicating bore 103 formed in a conduit 104 which is sealably located in a lumen 105 of the catheter 31 adjacent the distal end 33 of the catheter 31, and in part by a second communicating bore 106 which is formed by a part of the lumen 105. The lumen 105 of the catheter 31 is formed from an original lumen 107 which is configured for inflating the balloon 35 with a liquid inflating medium, which in this embodiment of the invention is also a saline solution. However, in this embodiment of the invention the lumen 107 is blocked at 108, so that the portion of the lumen 105 forming the second communicating bore 106 is isolated from the inflating part of the lumen 107. The inflating part of the lumen 107 terminates in the surface 62 of the catheter 31 within the balloon 35 for inflating thereof.

The lumen 105 extends from a first end 109 adjacent the distal end 33 of the catheter 31, and terminates in a second end 110 in the outer surface 62 of the catheter 31 within the balloon 35, and communicates with the hollow interior region 36 of the balloon 35. The conduit 104 extends into the lumen 105 from the first end 109 thereof and terminates in an end 111 intermediate the first and second ends 109 and 110 of the lumen 105. The conduit 104 is a tight fit in the lumen 105 and is sealably secured therein. The portion of the lumen 105 forming the second communicating bore 106 extends from the end 111 of the conduit 104 to the second end 110 of the lumen 105. The second communicating bore 106 communicates with the first communicating bore 103 through the end 111 of the conduit 104, to form with the first communicating bore 103 the communicating bore 102 extending from the first end 109 adjacent the distal end 33 of the catheter 31 to the second end 110. Accordingly, the communicating bore 102 comprising the first and second communicating bores 103 and 106 in series communicates the hollow interior region 36 of the balloon 35 with the gas chamber 55 of the pressure monitoring apparatus 101.

In this embodiment of the invention the lumen 105, and in turn the second communicating bore 106 is of circular transverse cross-section of constant diameter of approximately 1.31 mm, and the length of the second communicating bore 106 from the end 111 of the conduit 104 to the second end 110 is approximately 20 mm. In this embodiment of the invention the length of the conduit 104 from the first end 109 to the end 111, and in turn the length of the first communicating bore 103 is approximately 10 mm. The first communicating bore 103 is of circular transverse cross-section of constant diameter of approximately 0.5 mm.

Accordingly, in this embodiment of the invention the communicating bore 102 which extends from the first end 109 of the first communicating bore 103 adjacent the distal end 33 of the catheter 31 and terminates in the second end 110 of the second communicating bore 106 is of two different transverse cross-sectional areas, namely, the first communicating bore 103 of diameter of 0.5 mm, and the second communicating bore 106 of diameter of 1.31 mm, with a step change in the transverse cross-sectional areas between the first and second communicating bores 103 and 106 adjacent the end 111 of the conduit 104.

It has been found that as the liquid/gas interface meniscus 114 travels along the second communicating bore 106 the surface tension in the liquid/gas interface meniscus 114 is sufficient to prevent passage of the saline solution through or past the liquid/gas interface meniscus 114, and to prevent the passage of gas through or past the liquid/gas interface meniscus 114. However, as the liquid/gas interface meniscus travels in the direction of the arrow B, as the pressure of the saline solution in the balloon 35 increases further, the liquid/gas interface meniscus 114 travels into and along the first communicating bore 103 of the conduit 104. Since the diameter of the first communicating bore 103 of the conduit 104 is of 0.5 mm diameter there is no danger of the saline solution passing through or across the liquid/gas interface meniscus 114 nor is there any danger of the air passing through or across the liquid/gas interface meniscus 114.

In this embodiment of the invention the working length $L_w$ of the communicating bore 102 from the second end 110 is approximately 25 mm. In other words, the working length $L_w$ of the communicating bore 102 terminates in the first communicating bore 103 of the conduit 104 substantially half way between the first end 109 of the conduit 104 and the end 111 thereof.

Otherwise, the balloon catheter 100 and the pressure monitoring apparatus 101 and its use is similar to the balloon catheter 30 and the pressure monitoring apparatus 45 and its use described with reference to FIG. 3.

It will be appreciated that while the second end 109 of the communicating bore 102 in the embodiment of FIG. 7 has been described as terminating within the balloon 35 closer to the proximal end 40 than to the distal end 41 of the balloon, it is envisaged that in certain cases, the second end 109 of the communicating bore 102 may terminate in the balloon closer to the distal end 41 than to the proximal end 40, and indeed, in certain cases may terminate in the balloon substantially adjacent the distal end of the balloon.

Referring now to FIGS. 8 and 9, there is illustrated an endoscope according to another embodiment of the invention indicated generally by the reference numeral 120 which comprises a pressure monitoring apparatus also according to the invention and indicated generally by the reference number 121 located internally in a bore 123 of the endoscope 120 towards a distal end 124 of the endoscope 120 but spaced apart therefrom. The endoscope 120 is substantially similar to the endoscope 80 described with reference to FIGS. 5 and 6, and the pressure monitoring apparatus 121 is also substantially similar to the pressure monitoring apparatus 81 of the endoscope 80 of FIGS. 5 and 6, and similar components of the endoscope 120 and the pressure monitoring apparatus 121 are identified by the same reference numeral as those identifying the corresponding components of the endoscope 80 and the pressure monitoring apparatus 81.

The pressure monitoring apparatus 121 is secured in the bore 123 of the endoscope 120 by any suitable means, and in this embodiment of the invention is secured to the endoscope 120 in the bore 123 thereof by a suitable adhesive. In this embodiment of the invention the conduit 125, which is similar to the conduit 88 of the pressure monitoring apparatus 81 extends from a first end 122 in the gas chamber 85 and through the housing 83 of the pressure monitoring apparatus 121 through the bore 123 of the endoscope 120, and terminates at a second end 126 adjacent the distal end 124 of the bore 123 of the endoscope 120. The second end 126 of the conduit 125 is configured to releasably receive an external conduit 128 which in turn is configured to extend from the bore 123 of the endoscope 120 and longitudinally along an external surface 130 of the endoscope 120. The external conduit 128 terminates in a distal end 129. In this embodiment of the invention the external conduit 128 comprises a flexible conduit, which typically is disposable, and defines a bore 134. A clip 131 extending around the external surface 130 of the endoscope 120 secures the external conduit 128 to the endoscope 120. The second end 126 of the conduit 125 may terminate in a plain end which would be suitable to allow the external conduit 128 to be pushed slideably onto the second end 126 of the conduit 125, or alternatively, the external surface of the conduit 125 adjacent the second end 126 thereof may be provided with one or more barbs which would be configured to accommodate the external conduit 128 over the barbs and onto the conduit 125 adjacent the second end 126 thereof. The barbs would be configured to releasably retain the external conduit 128 on the second end 126 of the conduit 125, but would be configured in order to avoid inadvertent disengagement of the external conduit 128 from the conduit 125.

In this embodiment of the invention the communicating bore 133 of the conduit 125 is of circular transverse cross-sectional area of constant diameter of approximately 0.5 mm. The bore 134 of the external conduit 130, is of circular transverse cross-sectional area of diameter of approximately 1 mm. In this embodiment of the invention the total length of the communicating bore of the pressure monitoring apparatus 121 is formed by the communicating bore 133 of the conduit 125 and the portion of the bore 134 of the external conduit 128 from the second end 126 of the conduit 125 to the distal end 129 of the external conduit 128 in series.

It has been found that by providing the external conduit 128 with a bore 134 of diameter of approximately 1 mm, the liquid/gas interface meniscus formed in the bore 134 of the external conduit 128 is of sufficient surface tension to avoid any danger of the passage of liquid through or across the liquid/gas interface meniscus formed in the bore 134 of the external conduit 128, nor is there any danger of air passing through or across the liquid/gas interface meniscus formed in the bore 134 of the external conduit 128. Similarly, when the liquid/gas interface meniscus travels into the communicating bore 133 of the conduit 125 there is no danger of the liquid passing through or across the liquid/gas interface meniscus in the communicating bore 133 of the conduit 125, nor is there any danger of air passing through or across the liquid/gas interface meniscus in the communicating bore 133 of the conduit 125.

Otherwise, the endoscope 120 and the pressure monitoring apparatus 121 is similar to the endoscope 80 and the pressure monitoring apparatus 81 described with reference to FIGS. 5 and 6, and its use is likewise similar. Once the endoscope 120 with the external conduit 128 connected to the conduit 125 of the pressure monitoring apparatus and secured externally to the endoscope 120 by the clip 131 has been passed into the vessel, lumen or cavity in the body of the subject, with the distal end 124 of the endoscope 120 located in the vessel, lumen or cavity, and with to the distal end 129 of the external conduit 128 terminating in the vessel, lumen or cavity of the body of the subject, the pressure of the liquid in the vessel, lumen or cavity is monitored by the pressure monitoring apparatus 121.

It is envisaged that instead of providing the conduit 125 of the pressure monitoring apparatus 121 extending from the housing 83 of the pressure monitoring apparatus 121 to the distal end 124 of the bore 123 of the endoscope 120 and then attaching the external conduit 128 to the conduit 125, a transverse bore may be formed extending through a wall of the endoscope 120 from the bore 123 to the external surface 130 of the endoscope 120, which would accommodate the conduit 125 through the wall of the endoscope so that the conduit 125 would terminate adjacent the external surface of the endoscope.

While the pressure sensor has been described as comprising a piezoresistive sensor, any other suitable pressure sensor may be used, for example, a piezoelectric sensor, MEMS pressure sensors and the like.

While the communicating bores communicating the vessels, lumens, cavities and balloons of the balloon catheters, the endoscope and the pressure monitoring apparatus 1 with the gas chambers of the pressure monitoring apparatus have been described as comprising communicating bores of circular transverse cross-section, while this is desirable, it is not essential. In certain cases, it is envisaged that the communicating bores may be of square transverse cross-section, rectangular transverse cross-section or any other suitable transverse cross-section.

It will also be appreciated that the diameters of the communicating bores of the conduits may be of any suitable diameter, provided that the transverse cross-sectional area of the communicating bores and the inner surface defining the communicating bores are such that the surface tension induced in the liquid/gas interface meniscus is such as to prevent penetration of the liquid/gas interface meniscus by the gas or liquid, and to prevent passage of the gas or liquid past the liquid/gas interface meniscus. Typically, it is believed that conduits with communicating bores of diameter up to 1.31 mm may be used in conjunction with a saline solution/air interface meniscus. However, conduits of communicating bores of greater diameter may be used with liquid/air or liquid/gas interface meniscuses where the liquid has different physical properties, for example, is of a more viscous nature than that of a saline solution. Typically, it is envisaged that the maximum transverse cross-sectional dimension of the communicating bore would not exceed 5 mm, and preferably, would not exceed 3 mm, and ideally, should lie in the range of 0.1 mm to 2 mm, and preferably, should lie in the range of 0.1 mm to 1.5 mm. In general, it is envisaged that the transverse cross-sectional area of the communicating bore should not exceed 20 $mm^2$, and preferably should not exceed 7 $mm^2$, and ideally, should not exceed 1.35 $mm^2$. Ideally, it is believed that the transverse cross-sectional area of the communicating bore should lie in the range of 0.0079 $mm^2$ to 3.142 $mm^2$, and preferably, should lie in the range of 0.0079 $mm^2$ to 1.78 $mm^2$.

It is envisaged that the communicating bore communicating the gas chamber with the vessel, balloon or other lumen or cavity containing liquid, the pressure of which is to be monitored, has in some cases been described as comprising a bore of constant transverse cross-sectional area, and in the case of the embodiments of FIGS. 7 to 9 the communicating bore has been described as being formed by two bores arranged in series of different diameters, it is envisaged that where the communicating bore is not of constant transverse cross-sectional area over its total length, or at least over its working length, the transverse cross-sectional area may vary in step changes, or the transverse cross-sectional area may vary gradually without any step change. Needless to say, where the transverse cross-sectional area of the communicating bore varies in step changes, the number of step changes from one diameter to the next, and so on can be many. For example, the transverse cross-sectional area of the communicating bore may comprise three, four or more transverse cross-sectional areas, with each transverse cross-sectional area changing to the next transverse cross-sectional area in a step change. It will also be appreciated that the communicating bore may be of varying transverse cross-sectional area, and may comprise a combination of step changes from one transverse cross-sectional area to another, and one or more gradual changes of the transverse cross-sectional area. However, in general, it is envisaged that the portion of the communicating bore of the smallest transverse cross-section will be located adjacent the gas chamber, although in certain cases, it is envisaged that this may not always be the case. Furthermore, it will be appreciated that the transverse cross-sectional area of the communicating bore may not necessarily increase along the communicating bore from one end to the other, but may vary by increasing and decreasing and increasing again and decreasing again and so on from one end of the communicating bore to the other end.

Needless to say the length of the communicating bore and/or the sections of the different transverse cross-sections of the communicating bore may be any suitable length, which typically will be determined by the volume of the gas chamber and the transverse cross-sectional area of the communicating bore, as discussed above.

While the pressure monitoring apparatus has been described with gas chambers and communicating bores of specific dimensions, the gas chamber and the communicating bore may be of any other suitable dimensions.

While the pressure monitoring apparatus has been described for use in conjunction with a balloon catheter, the pressure monitoring apparatus may be used in conjunction with any catheter, for example, the balloon catheter as already described or indeed any other catheter with or without a balloon. Further, it will be appreciated that while the pressure monitoring apparatus has been described for use in conjunction with a catheter and an endoscope, which are essentially medical and/or surgical uses of the pressure monitoring apparatus, it will be immediately understood that the pressure monitoring apparatus may be used in conjunction with any system for monitoring pressure of a liquid in any vessel or lumen of any type other than a vessel, lumen or cavity in the body of a human or animal subject. In other words, the pressure monitoring apparatus according to the invention may be used for monitoring the pressure of a liquid in a vessel or conduit with no connection whatsoever to a human or animal subject. The vessel, for example, may be an industrial or domestic pressure vessel containing water or other liquid, the pressure of which is to be monitored, or the liquid the pressure of which is to be monitored could be a liquid flowing through a pipe in which the pressure of the liquid in the pipe is to be monitored.

It will be appreciated that the length of the communicating bore may be any suitable or desired length. However, it is important that the total length of the communicating bore should be greater than the working length of the communicating bore, where the working length of the communicating bore is the length along the communicating bore along which the liquid/gas interface meniscus travels as the pressure of the liquid being monitored varies. The working length of the communicating bore should be such as to contain the liquid/gas interface meniscus up to the maximum pressure which the liquid, the pressure which is being monitored could reach.

The volume of the gas chamber may be any desired volume, although, in general, it is believed that the volume of the gas chamber should not exceed 10 $mm^3$, and preferably, should not exceed 5 $mm^3$, and ideally, should not exceed 1 $mm^3$. In general, it is believed that the volume of the gas chamber should ideally lie in the range of 0.05 $mm^3$ to 0.5 $mm^3$.

It will however be appreciated that while in the embodiments of the invention described the communicating bore has been described as being a substantially straight elongated communicating bore, the communicating bore may be formed in a conduit which could be formed into a coil, which in the case of a catheter or balloon catheter, could be wrapped around the catheter or wrapped around the housing of the pressure monitoring apparatus. Alternatively, the conduit forming the elongated communicating bore could be formed in a coil within the housing, for example, in the gas chamber of the housing, and the second end of the communicating bore would extend through the housing from the gas chamber.

While the pressure monitoring apparatus has been described for use in conjunction with a balloon catheter and an endoscope, it will be readily apparent to those skilled in the art that the pressure monitoring apparatus may be used in conjunction with any system whereby it is desired to accurately monitor the pressure of a liquid with a relatively fast response time.

It is also envisaged that in certain cases, for example, in the case of a catheter or a balloon catheter, the gas chamber containing the gas may be formed integrally within the catheter and in which case the conduit may be dispensed with, and the communicating bore within which the liquid/gas interface meniscus travels would be formed by a communicating bore formed within the catheter, as for example, described with reference to FIG. 3. In this case the pressure sensor would be located in the catheter with the pressure monitoring interface communicating with the gas chamber.

It is also envisaged that in the case of a balloon catheter, the gas chamber may be formed in the catheter either adjacent the distal end, or at any other suitable location in the catheter, and the communicating bore would then extend from the gas chamber through the catheter and would communicate with the hollow interior region of the balloon. Needless to say, it is also envisaged that the housing may be located externally on the catheter within the hollow interior region defined by the balloon, and the conduit may extend along the catheter within the balloon. Alternatively, the conduit which forms the communicating bore may be wrapped around the catheter within the balloon.

It is also envisaged that in the case of the balloon catheter of FIG. 4 the conduit could extend along the catheter within the balloon and be secured to the catheter within the balloon. Alternatively, the conduit may be free floating within the balloon. Indeed, it is also envisaged that the conduit may be wrapped around the catheter within the balloon.

It is envisaged that in all cases, the pressure monitoring apparatus may be configured to releasably coupled or non releasably coupled to the catheter, the balloon catheter, the endoscope or any other system to which the pressure monitoring apparatus is coupled.

The invention claimed is:

1. A pressure monitoring apparatus for monitoring pressure in a liquid, the pressure monitoring apparatus comprising a pressure sensor having a pressure sensing interface communicating directly with a gas in a gas chamber, an elongated communicating bore communicating the gas chamber with the liquid, the pressure of which is to be monitored, the communicating bore having a working length along which a liquid/gas interface meniscus travels in response to pressure variation in the liquid, the working length of the communicating bore being of length to contain the travel of the liquid/gas interface meniscus within the working range of pressures being monitored, the transverse cross-sectional area of the communicating bore along the working length thereof being such as to prevent the passage of liquid past or through the liquid/gas interface meniscus, and to prevent the passage of gas past or through the liquid/gas interface meniscus;
 the pressure monitoring apparatus configured for coupling to a catheter, in which a balloon is mounted on the catheter, and the communicating bore communicates with the balloon.

2. An apparatus as claimed in claim 1 in which the transverse cross-sectional area of the communicating bore is smallest adjacent the gas chamber.

3. An apparatus as claimed in claim 1 in which the gas chamber comprises a fixed volume chamber.

4. An apparatus as claimed in claim 1 in which the volume of the gas chamber does not exceed 10 mm$^3$.

5. An apparatus as claimed in claim 1 in which the gas chamber comprises a sealed chamber.

6. An apparatus as claimed in claim 1 in which the apparatus comprises a housing defining the gas chamber.

7. An apparatus as claimed in claim 6 in which the pressure sensor is located in the housing with the pressure sensor interface communicating with the gas chamber.

8. An apparatus as claimed in claim 1 in which the communicating bore extends from the gas chamber through the housing.

9. An apparatus as claimed in claim 1 in which the communicating bore comprises an elongated bore extending through an elongated conduit, the conduit extending between a first end communicating with the gas chamber and a second end configured for extending into a vessel in which the liquid, the pressure of which is to be monitored is contained.

10. A catheter extending between a proximal end and a distal end, and comprising: a pressure monitoring apparatus for monitoring pressure in a liquid, the pressure monitoring apparatus comprising a pressure sensor having a pressure sensing interface communicating directly with a gas in a gas chamber, an elongated communicating bore extending from the gas chamber to communicate the gas chamber with the liquid, the pressure of which is to be monitored, the communicating bore having a working length along which a liquid/gas interface meniscus travels in response to pressure variation in the liquid, the working length of the communicating bore being of length to contain the travel of the liquid/gas interface meniscus within the working range of pressures being monitored, the transverse cross-sectional area of the communicating bore along the working length thereof being such as to prevent the passage of liquid past or through the liquid/gas interface meniscus, and to prevent the passage of gas past or through the liquid/gas interface meniscus;
 in which a balloon is mounted on the catheter, and the communicating bore communicates with the balloon.

11. A catheter as claimed in claim 10 in which the transverse cross-sectional area of the communicating bore is smallest adjacent the gas chamber.

12. A catheter as claimed in claim 10 any of in which the communicating bore extends from the gas chamber along a portion of the catheter and terminates adjacent an outer surface of the catheter.

13. A catheter as claimed in claim 10 in which the communicating bore comprises an elongated bore extending through an elongated conduit, the conduit extending between a first end communicating with the gas chamber and a second end configured for extending into a vessel in which the liquid, the pressure of which is to be monitored is contained.

14. A catheter as claimed in claim 13 in which the conduit extends externally along the catheter.

15. A catheter as claimed in claim 10 in which the gas chamber comprises a fixed volume chamber.

16. A catheter as claimed in claim 10 in which the volume of the gas chamber does not exceed 10 mm$^3$.

17. A catheter as claimed in claim 10 in which the gas chamber comprises a sealed chamber.

18. A catheter as claimed in claim 10 in which the gas chamber is formed in the catheter adjacent the distal end thereof.

19. A catheter as claimed in claim 10 comprising a housing which defines the gas chamber with the catheter.

* * * * *